United States Patent [19]
Girod-Vaquez et al.

[11] Patent Number: 5,262,405
[45] Date of Patent: Nov. 16, 1993

[54] METHOD OF IMPROVING BRONCHIAL MUCUS TRANSPORT

[75] Inventors: Sophie Girod-Vaquez; Edith Puchelle, both of Reims Cédex; Claude Galabert, Giens - Hyères; Jean-Marie Zam; Denis Pierrot, both of Reims Cédex, all of France

[73] Assignees: Synthelabo, Le Plessis Robinson; Inserm, Paris, both of France; a part interest

[21] Appl. No.: 658,330

[22] Filed: Feb. 20, 1991

[30] Foreign Application Priority Data

Feb. 20, 1990 [FR] France .................................. 90 01999

[51] Int. Cl.⁵ .............................................. A61K 31/66
[52] U.S. Cl. ......................................... 514/75; 514/76; 514/77; 514/78
[58] Field of Search ........................ 514/75, 76, 77, 78

[56] References Cited

U.S. PATENT DOCUMENTS

| | | | |
|---|---|---|---|
| 4,603,124 | 7/1986 | Takei et al. | 514/78 |
| 4,765,987 | 8/1988 | Bonte et al. | 514/78 |
| 5,032,585 | 7/1991 | Lichterberger | 514/78 |

OTHER PUBLICATIONS von Seefeld et al., Fortschr Med 102(39) 977–981 (Oct. 18, 1984).
Schlimmer et al. Eur J. Resp. Dis Suppl., 128 (Pt. 1): 318–321 (1985).

*Primary Examiner*—Douglas W. Robinson
*Assistant Examiner*—Jean C. Witz
*Attorney, Agent, or Firm*—Jacobson, Price, Holman & Stern

[57] ABSTRACT

A composition for use in the treatment of the obstruction of air ways comprising one or more phospholipids, alone or in association with excipients. This composition can be used in a method of treating the obstruction of air ways in a patient.

3 Claims, No Drawings

METHOD OF IMPROVING BRONCHIAL MUCUS TRANSPORT

The present invention relates to a pharmaceutical composition based on phospholipids.

The integrity of the respiratory mucosa epithelium depends on a balance between the factors of aggression and the mechanisms of defence at its disposal. The first line of defence of the tracheo-bronchial tree is the mucus which forms, at the surface of the respiratory epithelial cells, a protective film which is permanently mobilised by ciliary activity.

During inflammatory bronchitis, acute or chronic, the hypersecretion of mucus is accompanied by an alteration in its rheological properties, and an increase in the viscosity of the mucus and in its ability to adhere to the epithelial cells of the tracheo-bronchial wall. These abnormalities are manifested in a decrease in the mucociliary clearance and a stasis of mucus with bronchial obstruction. The transport of mucus by cough would then make up for the deficiency of the muco-ciliary clearance. It is therefore very important to preserve the efficiency of coughing, which depends on the viscous properties and the visco-elastic properties of the mucus and may also be greatly influenced by the interfacial properties between the mucus and the respiratory mucosa.

Up until now, therapies to correct the hypersecretion of mucus and its abnormalities have all developed on the basis of the fundamental concept that the treatment of hypersecretion ought primarily to address the alteration in the viscosity of the mucus considered as the only physical factor responsible for the stasis of the mucus and the bronchial obstruction. This concept has led to the development of numerous molecules with mucolytic activity which are active in vitro or in vivo and which are intended to normalise the hyperviscosity of the mucus.

In fact, during acute and/or chronic bronchial infections, secretions adhere firmly to the mucosa and their elimination by the ciliary activity, and even more by cough, can only be improved with difficulty by the prescription of a mucolytic therapy. Mucolytic agents, whether active in vivo or in vitro, act only on the fibrillar structure of the gel phase of the mucus and are inactive on the surface-active properties of the mucus.

Mucus possesses natural biochemical constituents among which are included the phospholipids which are capable of altering the mucus-mucosa interfacial properties.

It has been shown in numerous studies, in particular in acute respiratory distress syndrome of the new-born, that an immature lung which lacks surfactant, that is to say surface-active substance, can be made functional by the mere injection of artificial or natural surfactant. A large number of studies have also shown the presence of phospholipids, phosphatidylcholine in particular, in respiratory mucus and in expectorations, in healthy individuals as well as in individuals suffering from respiratory diseases accompanied by hypersecretion.

Phospholipids, including phospholipids with surface-active properties, have been credited with the role of stabilising the small air passages. They have also been credited, in their capacity as surface-active agents which are present at the sol phase-gel phase interface of the mucus and by virtue of their hydrophobic properties, with the role of regulating the water content of the sol phase. On the other hand, despite the hypotheses put forward, no study has shown how, by their presence in the sol phase-gel phase interface of the mucus, these phospholipids could effectively play a protective role towards respiratory mucosa and a lubricating role in the transport of the gel phase on the sol phase by the ciliary layer or by the mechanism of cough.

In bronchial pathology such as cysticfibrosis, previous studies have shown that in expectorations, some lipid fractions can be increased and significantly correlated with viscosity (cholesterol, glycosphingolipids, sphingomyelin) and could therefore be considered as "rigidifying" factors. On the other hand, it has been shown that some phospholipid fractions, like phosphatidylglycerol, are negatively correlated with viscosity. It appears that phosphatidylglycerol, although found in low quantities in bronchial secretions (10% of the total phospholipid), is capable of facilitating the transport of mucus by the movement of the cilia of the respiratory mucosa or by the phenomenon of cough by altering the visco-elastic properties of the mucus (reference: Galabert et al, Clin. Chim. Acta, 1987, 164:139–149).

We have studied the role of the different phospholipid fractions, known to reduce the surface tension at the alveolar level in the alterations of the surface-active properties of the mucus at the air passages. The works began with a study of patients affected with cysticfibrosis and chronic obstructive bronchopathy, in whom the content of phospholipid fractions in the expectorations and the surface properties of the phospholipid fractions were measured in parallel. The relationship between the biochemical data and the physical properties of the expectorations studied was analysed.

The collection of the expectorations was carried out avoiding any salivary contamination. The patients were divided into two groups composed of eighteen with cysticfibrosis and of sixteen with chronic bronchitis with hypersecretion and obstruction. The lipids were separated and identified using conventional techniques; for this, the expectorations were immediately frozen, then freeze-dried: the extraction of lipids was carried out on freeze-dried material.

The quantitative extraction of the lipids was carried out according to the method of Bligh E. G. and Dyer W. J.: A rapid method of total lipid extraction and purification. Can. J. Biochem. Physiol., 1959, 37, 911–917: 100 mg of freeze-dried material are rehydrated in 1 ml of distilled water. The lipids were then extracted with a chloroform/methanol mixture (1 v/2 v), then in a second chloroform/methanol mixture (1 v/1 v). After addition of water, the chloroform phase was separated off. Three complementary extractions by addition of 2.5 ml of chloroform were then carried out. The different chloroform phases were then combined, evaporated to dryness under nitrogen and $P_2O_5$, and then weighed before resuspending in solution in chloroform.

The total phospholipids and the phospholipid fractions, separated by two-dimensional thin layer chromatography, were determined by the method of Rouser et al. (Lipids, 1970, 5, 494–496) the principle of which is the micro-determination of phosphorus after mineralisation of the phospholipids by perchloric acid and separation by two-dimensional thin layer chromatography.

From the determination of the phospholipids in these secretions, it was shown that the total phospholipids were significantly higher in cysticfibrosis than in chronic obstructive bronchitis (4.40% against 2.96% of dry weight of mucus respectively (p<0.01)). The relative percentage of phosphatidylcholine and phosphatidylglycerol was significantly lower (p<0.001) in cysticfibrosis than in chronic obstructive bronchopathy (Table I). The relative percentages of sphingomyelin and phosphatidyl-serine+phosphatidylinositol were significantly higher (p<0.001) in cysticfibrosis than in chronic obstructive bronchitis (Table I).

TABLE I

| Percentage of the main phospholipid fractions relative to the total lipids | | | | |
|---|---|---|---|---|
| | PG | PC | SM | PS + PI |
| Cystiofibrosis | 4.41 | 36.32 | 22.24 | 15.10 |
| Chronic bronchitis | 7.48 | 46.47 | 12.44 | 11.76 |

PC:phosphatidylcholine; PG:phosphatidylglycerol; SM:sphingomyelin; PS+PI:phosphatidylserine+phosphatidylinositol.

In the case of cysticfibrosis, where the secretions are very adhesive and very viscous, fewer surface-active fractions (phosphatidylcholine, phosphatidylglycerol) and more "rigidifying" fractions (sphingomyelin) were found in the expectorations than in the other bronchopathies.

A physical study of these secretions has been carried out in parallel. The physical property chosen was the wettability of the secretions which provides information on the ability of a secretion to wet a surface. The wettability is estimated by a physical parameter called the contact angle. The contact angle can be defined as the angle between the tangent to a liquid droplet placed on a solid base (at the liquid-air interface) and the surface of the solid (at the solid-liquid interface) at the triple point Tp.

The contact angle depends on the solid, the nature of the liquid and the interaction between them. We have studied the behaviour of bronchial secretions when they are put into contact with a support which simulates the bronchial mucosa. The contact angle is an index of wettability which provides information on the surface-active properties of the liquid for a given solid: the larger the contact angle, the less the liquid spreads and the less wetting it is.

A technique for automatically measuring the contact angle based on image analysis coupled with computer analysis has been developed. During measurements of the wettability of the secretions, it was chosen to measure the contact angle of a calibrated (5 μl) secretion droplet which was put into contact with a perfectly plain glass support, electronegatively charged and placed in a container saturated with water vapour in order to avoid dehydration processes (reference: S. Girod et al. I.T.B.M, 1988, 9 402–412).

The phosphatidylglycerol appears to be an important phospholipid which controls the wettability of bronchial secretions and which is capable of influencing their transport and their behaviour when they are in contact with the mucosa. We therefore studied the influence of various phospholipids on the wettability properties of the respiratory mucus and on its ability to be mobilised and transported by the mechanism of cough. An experiment intended to study the effect, in vitro, of various phospholipid fractions on the wetting ability and the transport by cough of mucus considered as "normal" was therefore carried out.

The mucus was taken from frog palate mucosa which is considered to be a good representative model of human respiratory mucosa. The wettability of these mucus was measured as previously described. The clearance of these mucus by cough was measured using a cough machine. The principle of this machine is as follows: the support on which the mucus droplet is deposited is used as the base for a plexiglas tube which simulates the trachea. The plexiglas tube of rectangular section (20 mm×10 mm) is connected to a container which is closed by means of an electrovalve. The pressure inside the container is brought to 0.6 bar, then the electrovalve is opened and the air flow rate to which the droplet is subjected is 6 l/s. The displacement of the droplet on the support under the influence of the air current thus produced, which simulates the mechanism of cough, is measured.

The supports used were either simple glass plates or glass plates covered with a monolayer of phospholipids using a Langmuir film balance: 10 mg of each phospholipid fraction was dissolved in a chloroform/methanol mixture (9:1) and 16 μl of this solution was deposited in the basin of the film balance filled with triple-distilled water. A Teflon barrier compressed the phospholipid film until obtention of the collapsing pressure specific to each phospholipid, at which all the phospholipid molecules are in contact without holes in the monolayer. The glass support previously immersed in the basin was then withdrawn at a constant speed and, at the same time, the Teflon barrier advances so as to keep constant also the surface tension of film thus removed; the glass support thus obtained had on its surface an oriented monolayer of phospholipids attached to the glass by their polar heads and exposing their non-polar groups to the air (in contact with the mucus).

The phospholipids chosen for this study were phosphatidylglycerol (diC$_{18:1}$) (Sigma 9399) and phosphatidylglycerol (diC$_{18:0}$) (Sigma 9524): these fractions therefore had the same polar head, the same fatty acid chain length but differ from each other in the degree of saturation. Glass plates not covered with phospholipids were kept as controls.

It emerges that phosphatidylglycerol (diC$_{18:0}$) significantly improves the clearance of frog mucus by cough and significantly decreases its wettability, in comparison with uncovered glass plates (p<0.001 and p<0.01) or even with glass plates covered with phosphatidylglycerol (diC$_{18:0}$) (p<0.001 and p<0.01). The phosphatidylglycerol (diC$_{18:0}$) appears to be the phospholipid fraction which, by reducing the adhesive properties of the mucus, improves its clearance by cough (the most lubricating fraction).

Phosphatidylcholine in the form of dipalmitoylphosphatidyl-choline (diC$_{16:0}$) was also studied with respect to the wettability and the transporting ability by cough.

In view of these studies, the invention comprises a composition for use in the treatment of the obstruction of air passages comprising one or more phospholipids, alone or in association with excipients. The phospholipid or phospholipids may be chosen from among phosphatidylcholines, phosphatidylglycerols and phosphatidic acids.

The phospholipids use in accordance with the invention may comprise identical or different, saturated or unsaturated acyl radicals.

The phospholipids used in the compositions in accordance with the invention more particularly comprise two identical saturated acyl radicals.

The above mentioned phospholipids preferably comprise, by way of acyl radicals, the saturated radicals palmitoyl $C_{16:0}$ and stearoyl $C_{18:0}$ and/or the unsaturated radicals oleoyls $C_{18:1}$ and $C_{18:2}$; and most preferably comprise dipalmitoylphosphatidylcholine, distearoylphosphatidylcholine, phosphatidyl-glycerol $diC_{18:0}$, phosphatidyl-glycerol $diC_{18:1}$ and phosphatidylglycerol $diC_{16:0}$.

The acyl radicals of the phospholipids may optionally contain several double bonds.

The phospholipids may be used alone or, preferably, mixed with one another in variable proportions.

The compositions in accordance with the invention may be provided in the form of micellar suspensions or in the form of liposome suspensions. They can be administered orally or aerially, for example by inhalation (in the form of aerosols) or by instillation.

The compositions in accordance with the invention may also contain therapeutic agents known for their activity in the field of bronchopulmonary diseases and which are capable of having a specific activity on the bronchial mucosa.

In particular, it is possible to combine the phospholipids, in the form of micellar suspensions (or emulsions) or in the form of liposome suspensions, as instillations or as aerosols, with the following compounds:

agents protecting against free radicals such as cysteine derivatives or superoxide dismutase, antibacterial substances such as lysozyme or asialo-GMI-ganglioside growth factors such as insulin, retinoic acid derivatives, epithelium growth factor (or EGF) and platelet derived growth factor (or PDGF), repair factors such as glycyl-L-histidyl-L-lysine and other peptides purified from epithelial or mesenchymatous cells, mucus-hydrating agents such as ATP.

The compositions of the invention are used for the treatment of bronchopulmonary diseases.

The invention also relates to a method of treating the obstruction of respiratory airways in a patient, which comprises administering to the patient a therapeutically effective amount of a composition comprising one or more phospholipids, as described above.

We claim:

1. A method of improving bronchial mucus transport in a patient in need thereof which comprises administering to the patient a therapeutically effective amount of phosphatidylglycerol ($diC_{18:0}$).

2. The method according to claim 1, wherein the phosphatidylglycerol ($diC_{18:0}$) is provided in the form of a micellar suspension.

3. The method according to claim 1, wherein the phosphatidylglycerol ($diC_{18:0}$) composition is provided in the form of a liposome suspension.

* * * * *